(12) United States Patent
Machovina et al.

(10) Patent No.: US 12,129,638 B2
(45) Date of Patent: Oct. 29, 2024

(54) FILTRATION ASSEMBLY FOR REDUCING MALAODORS IN AIR AND AEROSOLIZED WASTE FROM TOILETS

(71) Applicants: Brian L. Machovina, Coral Gables, FL (US); Eileen McHale, Avon Lake, OH (US)

(72) Inventors: Brian L. Machovina, Coral Gables, FL (US); Eileen McHale, Avon Lake, OH (US)

(73) Assignee: Hound Tech LLC, Coral Gables, FL (US)

( * ) Notice: Subject to any disclaimer, the term of this patent is extended or adjusted under 35 U.S.C. 154(b) by 191 days.

(21) Appl. No.: 17/968,759

(22) Filed: Oct. 18, 2022

(65) Prior Publication Data

US 2023/0038314 A1 Feb. 9, 2023

Related U.S. Application Data

(63) Continuation-in-part of application No. 17/968,731, filed on Oct. 18, 2022, and a continuation-in-part of application No. 16/362,063, filed on Mar. 22, 2019, now Pat. No. 11,473,286, which is a continuation-in-part of application No. 15/909,344, filed on Mar. 1, 2018, now abandoned.

(Continued)

(51) Int. Cl.
*E03D 9/00* (2006.01)
*A61L 2/10* (2006.01)
*E03D 9/05* (2006.01)

(52) U.S. Cl.
CPC ............... *E03D 9/005* (2013.01); *A61L 2/10* (2013.01); *E03D 9/05* (2013.01); *A61L 2202/11* (2013.01)

(58) Field of Classification Search
CPC ... E03D 9/052; B01D 46/0028; B01D 46/0038; B01D 46/0047; B01D 46/4245; B01D 2279/65; B01D 2253/102; B01D 53/0407; B01D 2257/90; B01D 2259/4508; B01D 2259/4541; A47K 13/307
USPC ............................. 4/209, 219, 306, 347, 477
See application file for complete search history.

(56) References Cited

U.S. PATENT DOCUMENTS 3,066,317 A 12/1962 Cawiezel
3,849,808 A 11/1974 Olson et al.
(Continued)

FOREIGN PATENT DOCUMENTS

CA 2943135 A1 * 3/2017 ........... A47K 13/307
CN 105507397 A 12/2017
(Continued)

*Primary Examiner* — Lori L Baker
(74) *Attorney, Agent, or Firm* — Tucker Ellis LLP

(57) ABSTRACT

An assembly for filtering toilet bowl odors including first and second housings respectively disposed in spaced relation to and in fluid communication with the toilet bowl. A conduit connects interiors of the first and second housings in fluid communication with one another. A fan assembly is mounted within said first housing in fluid communicating relation with the second housing, via the conduit, and is disposed and structured to define a path of fluid flow extending from an inlet of said second housing, through said conduit and a filter assembly, disposed in the first housing and/or second housing, to the exterior of said first housing, concurrent to activation of the fan assembly.

20 Claims, 10 Drawing Sheets

Related U.S. Application Data

(60) Provisional application No. 63/307,330, filed on Feb. 7, 2022, provisional application No. 62/726,624, filed on Sep. 4, 2018, provisional application No. 62/465,963, filed on Mar. 2, 2017.

(56) References Cited

U.S. PATENT DOCUMENTS

| | | | |
|---|---|---|---|
| 4,117,559 A | 10/1978 | Boyle | |
| 4,726,078 A | 2/1988 | Carballo et al. | |
| 4,944,045 A * | 7/1990 | Agelatos | E03D 9/052 4/213 |
| 5,488,741 A * | 2/1996 | Hunnicutt, Jr. | E03D 9/052 4/352 |
| 5,555,572 A * | 9/1996 | Hunnicutt, Jr. | E03D 9/052 4/352 |
| 5,671,484 A | 9/1997 | Lee, III | |
| 5,727,262 A | 3/1998 | Littlejohn | |
| 6,003,157 A | 12/1999 | Bruyere | |
| 6,260,214 B1 | 7/2001 | Smith | |
| 6,588,025 B1 | 7/2003 | Helmolt | |
| 6,678,900 B2 | 1/2004 | Ware | |
| 6,760,928 B1 | 7/2004 | Rodriguez | |
| 8,161,579 B2 | 4/2012 | Denkewicz, Jr. et al. | |
| 8,490,221 B1 | 7/2013 | Conde | |
| 10,881,936 B2 | 1/2021 | Machovina et al. | |
| 11,473,286 B2 | 10/2022 | Machovina et al. | |
| 2002/0069456 A1 | 6/2002 | Kuzniar | |
| 2002/0189008 A1 | 12/2002 | Hipponsteel | |
| 2003/0163863 A1 | 9/2003 | Stone | |
| 2003/0177568 A1 * | 9/2003 | Chasen | E03D 9/052 4/213 |
| 2003/0192112 A1 | 10/2003 | Ware | |
| 2005/0166305 A1 * | 8/2005 | Green | A47K 13/307 4/217 |
| 2006/0064803 A1 | 3/2006 | Wang | |
| 2007/0234469 A1 | 10/2007 | Denkewicz et al. | |
| 2007/0256219 A1 * | 11/2007 | Ellinger | E03D 9/052 4/213 |
| 2008/0000017 A1 | 1/2008 | Littrell et al. | |
| 2008/0083056 A1 | 4/2008 | Damianoe et al. | |
| 2009/0056007 A1 * | 3/2009 | Pham | E03D 9/052 4/347 |
| 2009/0158515 A1 | 6/2009 | Bruno | |
| 2010/0199413 A1 * | 8/2010 | Pollack | E03D 9/052 4/213 |
| 2011/0047689 A1 * | 3/2011 | Gianelloni | E03D 9/052 4/348 |
| 2012/0186007 A1 | 7/2012 | Perez | |
| 2013/0152790 A1 | 6/2013 | Ingledew et al. | |
| 2013/0160197 A1 * | 6/2013 | Conley | F24F 7/065 4/347 |
| 2013/0269091 A1 * | 10/2013 | Sollami | A47K 13/307 4/213 |
| 2014/0137317 A1 * | 5/2014 | Sollami | E03D 9/05 4/213 |
| 2014/0304903 A1 * | 10/2014 | Cogswell | E03D 9/052 4/314 |
| 2016/0010318 A1 * | 1/2016 | Sollami | A47K 13/307 4/213 |
| 2017/0014009 A1 | 1/2017 | Smith | |
| 2018/0154297 A1 | 6/2018 | Maletich et al. | |
| 2019/0218762 A1 * | 7/2019 | Machovina | B01D 53/02 |
| 2019/0292760 A1 * | 9/2019 | Finkbeiner | E03D 9/052 |
| 2023/0038314 A1 * | 2/2023 | Machovina | A61L 2/10 |

FOREIGN PATENT DOCUMENTS

| | | | |
|---|---|---|---|
| CN | 212506590 | 2/2021 | |
| DE | 4009162 | 11/1990 | |
| JP | 1999501372 | 2/1999 | |
| JP | 2000160628 | 6/2000 | |
| JP | 2001262663 | 9/2001 | |
| JP | 2021536331 | 12/2021 | |
| WO | WO-2010091390 A2 * | 8/2010 | E03D 9/052 |
| WO | WO2020050911 | 3/2020 | |
| WO | WO-2020050911 A1 * | 3/2020 | A61L 9/014 |
| WO | WO-2023049436 A1 * | 3/2023 | A47K 13/30 |

* cited by examiner

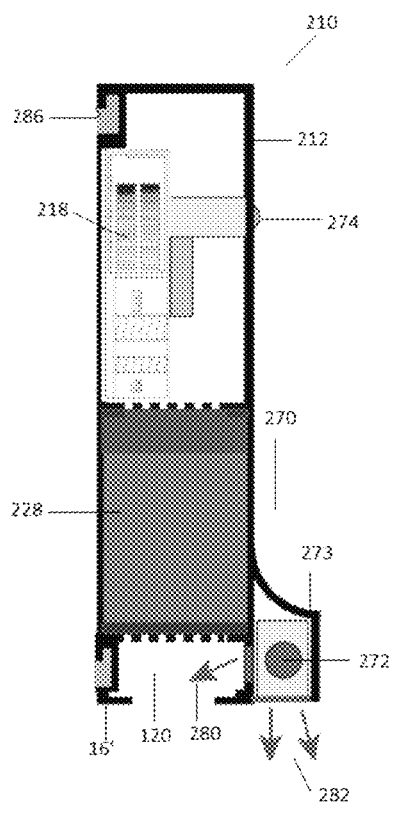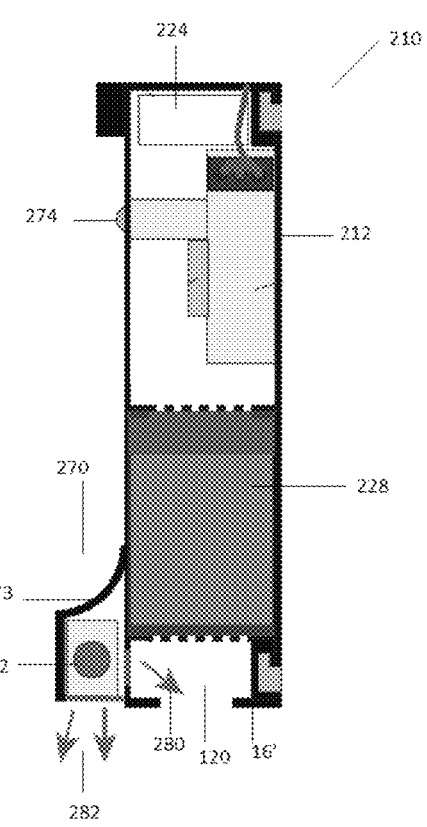

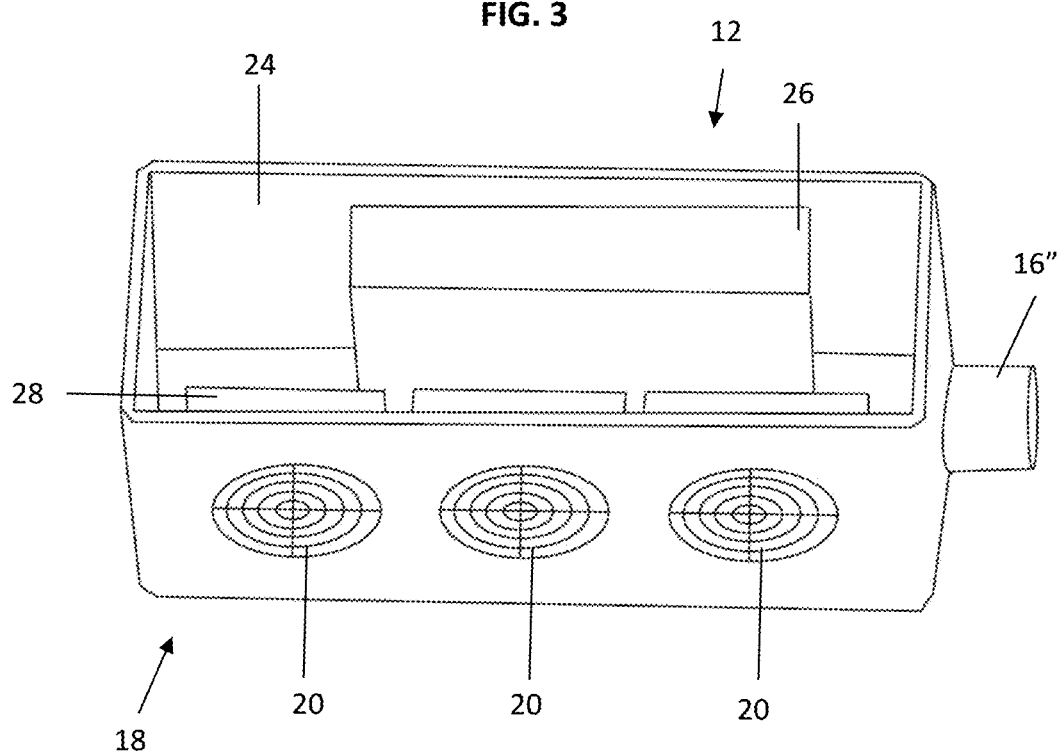

FIG. 4A
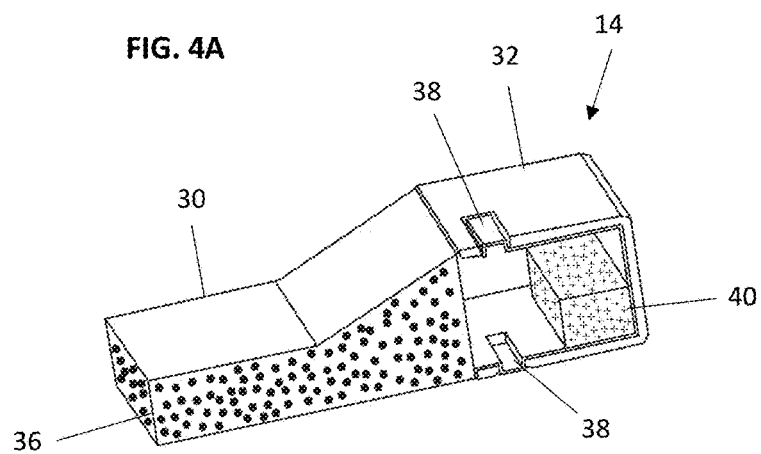
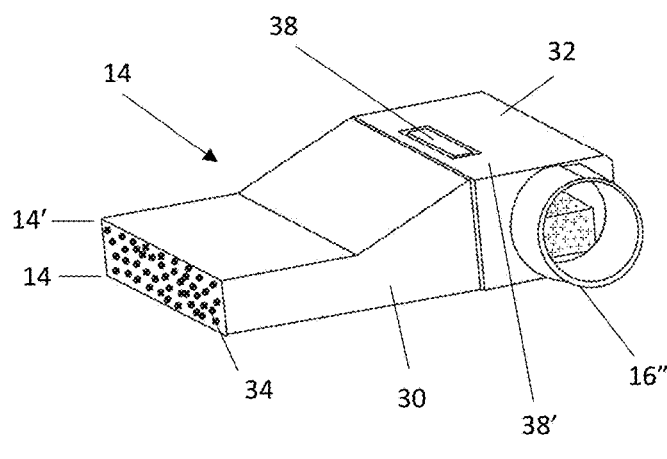
FIG. 4B
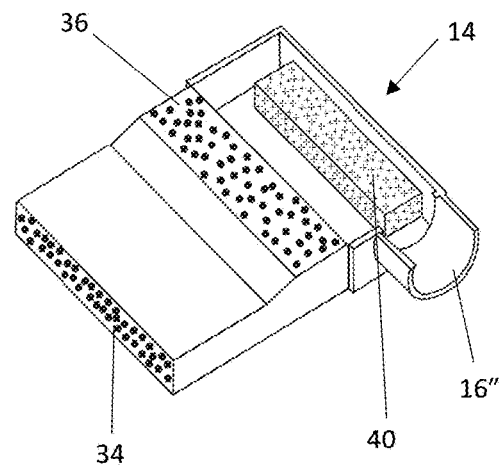
FIG. 4C

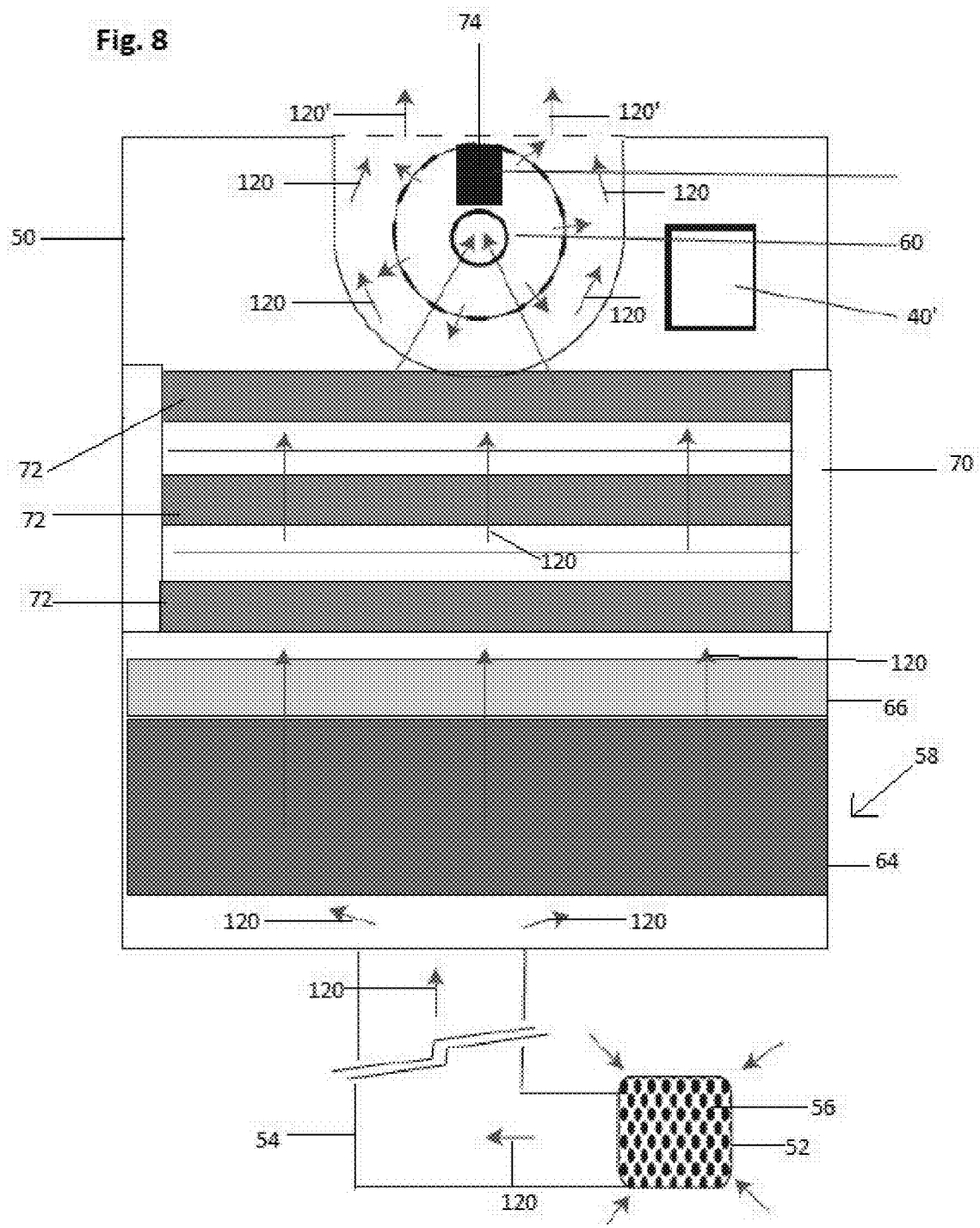

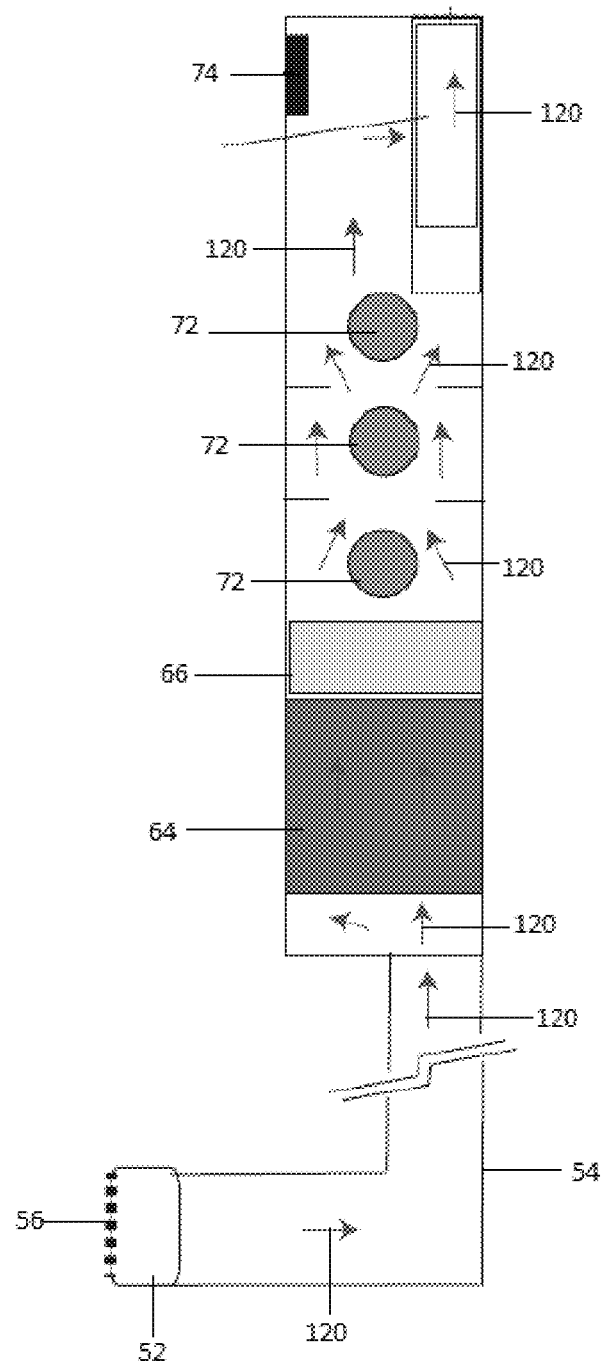

FILTRATION ASSEMBLY FOR REDUCING MALAODORS IN AIR AND AEROSOLIZED WASTE FROM TOILETS

CLAIM OF PRIORITY

The present application is a Continuation-In-Part application of a previously filed, now pending application having U.S. application Ser. No. 17/968,731, and which has a filing date of Oct. 18, 2022, to which a claim of priority is made under 35 U.S.C. Section 119(e) to a provisional patent application having U.S. Application No. 63/307,330 and a filing date of Feb. 7, 2022, which are incorporated by reference herein. The present application is also Continuation-In-Part application of previously filed, now pending application having U.S. application Ser. No. 16/362,063, which was filed on Mar. 22, 2019, to which a claim of priority is made under 35 U.S.C. Section 119(e) to a provisional patent application having U.S. Application No. 62/726,624, and a filing date of Sep. 4, 2018, which are incorporated by referenced herein, and which is a Continuation-In-Part application of a previously filed application having U.S. application Ser. No. 15/909,344, which was filed on Mar. 1, 2018, to which a claim of priority is made under 35 U.S.C. Section 119(e) to a provisional patent application having U.S. Application No. 62/465,963, which was filed on Mar. 2, 2017, all of which are incorporated herein by reference.

FIELD OF THE INVENTION

This invention is directed to an assembly for the filtration and other processing of air and aerosolized fluid issuing from the interior of a toilet bowl.

DESCRIPTION OF THE RELATED ART

The odor of human waste released by people into a toilet bowl can enter the general surrounding area and remain suspended during toilet use and for periods of time post toilet use. This can be unpleasant to the present toilet user, to others located in the nearby environment, or to others that enter the area later to use the same toilet.

Air purifiers and air filters are widely used in interior spaces such as homes and offices to minimize the amount of dust, allergens, and micro-organisms that are present in the air. These systems typically include a fan for circulating air and a mechanical filter disposed in an air path to filter or purify air flowing there through. Larger fans, air purifiers and/or air filters tend to be more effective due to the large volume of air they can remove, filter and/or purify at a given time. However, larger units of this type are usually obtrusive and take up a considerable amount of space in the home or office. Further, these larger systems may require more electricity and are often loud due to the size of the fans included in the system.

Although fans, air purifiers and air filters may provide a solution to combating the presence of contaminants such as dust, allergens and micro-organisms, they may lack the means to effectively remove the odors from the air. Individuals are well aware of the offensive odors that may be released from flatulence, feces, or urine. These odors can be disruptive and unpleasant to individuals located in the vicinity of such odors. When unpleasant odors are present in the air, individuals usually commonly use air freshener sprays, plug in air fresheners or the like, to "cover-up" the unpleasant odor with a more pleasant scent. However, this tactic merely masks the presence of the unpleasant odor and does nothing to actually remove the odor.

Additionally, the use of air fresheners or sprays presents an unfortunate problem because an individual must first come in contact with the unpleasant odor before these devices can be used to mask the scent. Furthermore, while the scent of air fresheners, sprays, etc. may provide a more pleasant odor, as compared to odors released from flatulence, feces or urine, some individuals may not enjoy still not enjoy or even be able to tolerate such fragrances.

Accordingly, there is a need for an air filter and/or odor processing assembly and/or system operative to withdraw, filter and otherwise treat or process odors, specifically including those emanating from flatulence, defecation and/ or urination, directly from a toilet bowl airspace. Treatment of such odors thereby eliminate or significantly reduce the release thereof into the surrounding airspace. Such processing and/or treatment of such odors may include passing air or aerosolized fluid containing such odors across a filter assembly operatively structured to absorb the odors. In addition, a proposed assembly and/or system of the type referred to may also include a filter assembly capable of removing aerosolized particles contained in a "toilet plume".

Moreover, the treatment or processing of fluid removed from the interior of a toilet bowl may also include sterilizing capabilities operative to remove germs, bacteria, etc. prior to reaching the air or space surrounding the toilet. In addition, modification of certain structural and operative features may serve to enhance the versatility of an improved odor elimination assembly and/or system, thereby enabling its use in both domestic and commercial environments. Finally, a proposed and improved toilet odor processing assembly and or system which overcomes known disadvantages of the type set forth above, should be designed to be inexpensive, easily serviceable and convenient enough to change install and maintain.

SUMMARY OF THE INVENTION

The present invention is directed to an assembly for filtering/removing odors issuing from a toilet bowl. In addition, one or more preferred embodiments of the filter assembly is operative to filter/remove odors from air as well as processing aerosolized fluid, resulting from a "toilet plume" which may develop when the toilet is flushed. As will be explained in greater detail hereinafter, different ones of a possible plurality of embodiments of the filtering assembly may be structurally and operatively adapted for use in either a domestic environment or commercial environment and/or both.

Accordingly, at least one preferred embodiment of the present invention comprises a first housing disposed in spaced relation to the toilet bowl and having a fan assembly disposed therein. A second housing is disposed in adjacent relation to the toilet bowl and includes an inlet disposed in fluid communication with the toilet bowl interior. The second housing includes a filter segment and a connector segment removably connected to one another, wherein a filter is fixedly disposed and retained within the filter segment. Moreover, the fixedly retained filter is disposed adjacent to and/or otherwise downstream of the inlet, in receiving relation to fluid passing into the interior of the filter segment of the second housing through the inlet.

An elongated conduit is disposed in interconnecting, fluid communicating relation between interiors of the first and second housings. The elongated conduit is disposed and structured to direct the flow of fluid entering the second housing through the inlet and retained filter in the filter segment, through the interior of the connecting segment and along the length of the conduit into first housing. Accordingly, a path of fluid flow is established from the inlet, through the filter in the filter segment of the second housing, through the connector segment, along the length of the conduit and into and through the interior of the first housing, concurrent to activation of the aforementioned fan assembly, within the first housing.

Further, the fan assembly is disposed and structured, when activated, to direct fluid flow from the interior of the first housing outwardly therefrom to an exterior thereof. As a result, air/fluid passing into the second housing, through the aforementioned inlet will be sufficiently processed, at least in terms of removing or significantly eliminating odor contained therein, for subsequent entry back into the space or area surrounding the toilet.

Additional structural and operative features of at least one embodiment of the filtering assembly includes the aforementioned fan assembly, being disposed in the first housing and comprising at least one or in the alternative a plurality of fan units. As such, when activated, the one or more fan units are individually and/or collectively disposed to direct fluid flow along the path of travel from the interior of the second housing, through the conduit, and through and outwardly from the interior of the first housing.

As indicated, the filter segment and the connector segment collectively and at least partially defining the second housing are removably connected to one another, such that the interiors thereof are in direct fluid communication. The removable connection therebetween preferably comprises, but is not limited to, an inner end of both the filter segment and connector segment being cooperatively structured to accomplish removable attachment to one another. Moreover, in at least one embodiment cooperative structural features of the inner ends of the filter and connector segments of the second housing facilitate a telescopic connection therebetween as well as a "snap-fit" attachment. This enables a quick and easy detachment from one another.

In association therewith, another practical advantage of this embodiment of the filter assembly includes the filter segment and the fixedly retained filter therein being collectively detached from the connector segment and structured for disposal after a predetermined period of use. A new filter segment and enclosed filter may then be connected to the existing and/or same connector segment for continued and prolonged use of the remainder of the filter assembly.

In order to facilitate packaging, shipping, installation and maintenance of the filter assembly, the elongated conduit may be removably attached to both the first housing and to the second housing, the latter via the connector segment.

Yet additional features may include the inclusion of a secondary filter disposed within the interior of the first housing and further positioned upstream of the fluid entering the first housing through the conduit and downstream of the fan assembly. As a result, additional filtering of the fluid passing into the inlet of the filter segment of the second housing and therefrom along the conduit into the first housing will be additionally filtered to further facilitate removal of odor. A scent releasing structure or device may also be included, preferably, but not necessarily, within the first housing.

The above noted embodiment of the filter assembly for home use, in a domestic environment, may include a manual on/off user interface. Such interface may be preferably disposed in an exposed location on the exterior of the first housing. Further control circuitry may be contained in the first housing, in the form of a printed circuit board or other appropriate control circuitry. Further, the control circuitry may include time delay capabilities facilitating the automatic turnoff of the fan assembly after the expiration of a predetermined period of time from its manual activation. In the alternative and or in addition thereto the manual on/off user interface may be manipulated to extend the activation of the fan assembly or to cease activation thereof before the predetermined time period has elapsed. In cooperation therewith, this embodiment may preferably be operated by and appropriately powered battery pack, in order to facilitate quick and easy installation, maintenance, etc.

One or more additional embodiments of the filter assembly of the present invention may be structurally and operatively similar to the above described embodiment, but may be more adapted for use in a commercial environment. As such, the additional one or more embodiments of the filter assembly includes a first housing disposed in spaced relation to the toilet bowl and including a filter assembly contained therein. A second housing is disposed adjacent the toilet bowl and includes an inlet disposed in fluid communicating relation with the interior of the toilet bowl. An elongated conduit may be disposed in interconnecting, fluid communicating relation between the interiors of the first and second housings.

Further, a fan assembly is mounted within the first housing in fluid communication with the conduit and through the conduit, in fluid communication with the interior of the second housing and the inlet associated therewith. Therefore, the fan assembly is disposed and structured to direct fluid flow from the conduit through the interior of the first housing and outwardly therefrom to an exterior of the first housing, subsequent to being processed. Accordingly, an activation of the aforementioned fan assembly, within the interior of the first housing, defines or establishes a path of fluid flow extending from said inlet of the second housing, through the conduit and into the interior of the first housing, through the filter assembly, to the exterior of the first housing and back into the space, area or environment surrounding the toilet.

Yet additional features of the additional one or more embodiments of the filter assembly, which may render it more adaptable for use in a commercial environment, comprises the filter assembly including a first filter unit and a second filter unit, both located upstream of the conduit and downstream of the fan assembly. The first filter unit may be a carbon-based filter primarily operative to remove odors from air/gas passing there through. The second filter unit of the filter assembly is preferably structured to process aerosolized fluid and any particulate matter contained therein and may be comprise an HEPA filter. As indicated, aerosolized fluid may result from the toilet being flushed and the creation of a "toilet plume", possibly containing odor causing particulate waste material.

In addition to the filter assembly including, the first and second filter units, a fluid sterilizing assembly may be disposed within the first housing, upstream of the conduit and downstream of the fan assembly. The sterilizing assembly may comprise at least one or in the alternative a plurality of ultraviolet (UV) lights disposed in the path of fluid flow exiting from the aforementioned filter assembly, or otherwise passing through the interior of the first housing.

Possible installation and use of this additional embodiment of the filter assembly of the present invention may include the inclusion of a sensor assembly such as, but not limited to a motion sensor. The sensor assembly may be preferably mounted on the first housing and be positioned/ oriented to detect the presence of an individual utilizing the toilet. The sensor assembly may be further structured to activate the fan assembly while an individual remains in a predetermined detection zone. Automatic shutoff of the fan assembly will result upon an absence of an individual from the aforementioned detection zone. Powering of the fan assembly may best be accomplished by a direct wired connection to a conventional AC power source typically associated with most commercial locations which include restrooms and or semi-public toilet facilities.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 2C is a side interior schematic representation of another embodiment of the present invention.

FIG. 2D is a side interior schematic representation of the embodiment of FIG. 2C.

FIG. 3 is a perspective interior view of a first housing of the embodiment of the assembly as represented in FIG. 1.

FIG. 4A is an exterior perspective view of a second housing of the embodiment of the assembly as represented in FIG. 1

FIG. 4B is a longitudinal sectional view in perspective of the interior of the embodiment of FIG. 4A.

FIG. 4C is a transverse sectional view in perspective of the interior of the embodiment of FIGS. 4A and 4B.

FIG. 8 is an interior view in schematic form of the embodiment of the assembly as represented in FIG. 6.

FIG. 9 is a longitudinal sectional view of the interior of the schematic representation of the embodiment of FIG. 8.

Like reference numerals refer to like parts throughout the several views of the drawings.

DETAILED DESCRIPTION OF THE PREFERRED EMBODIMENT

Figure 1:
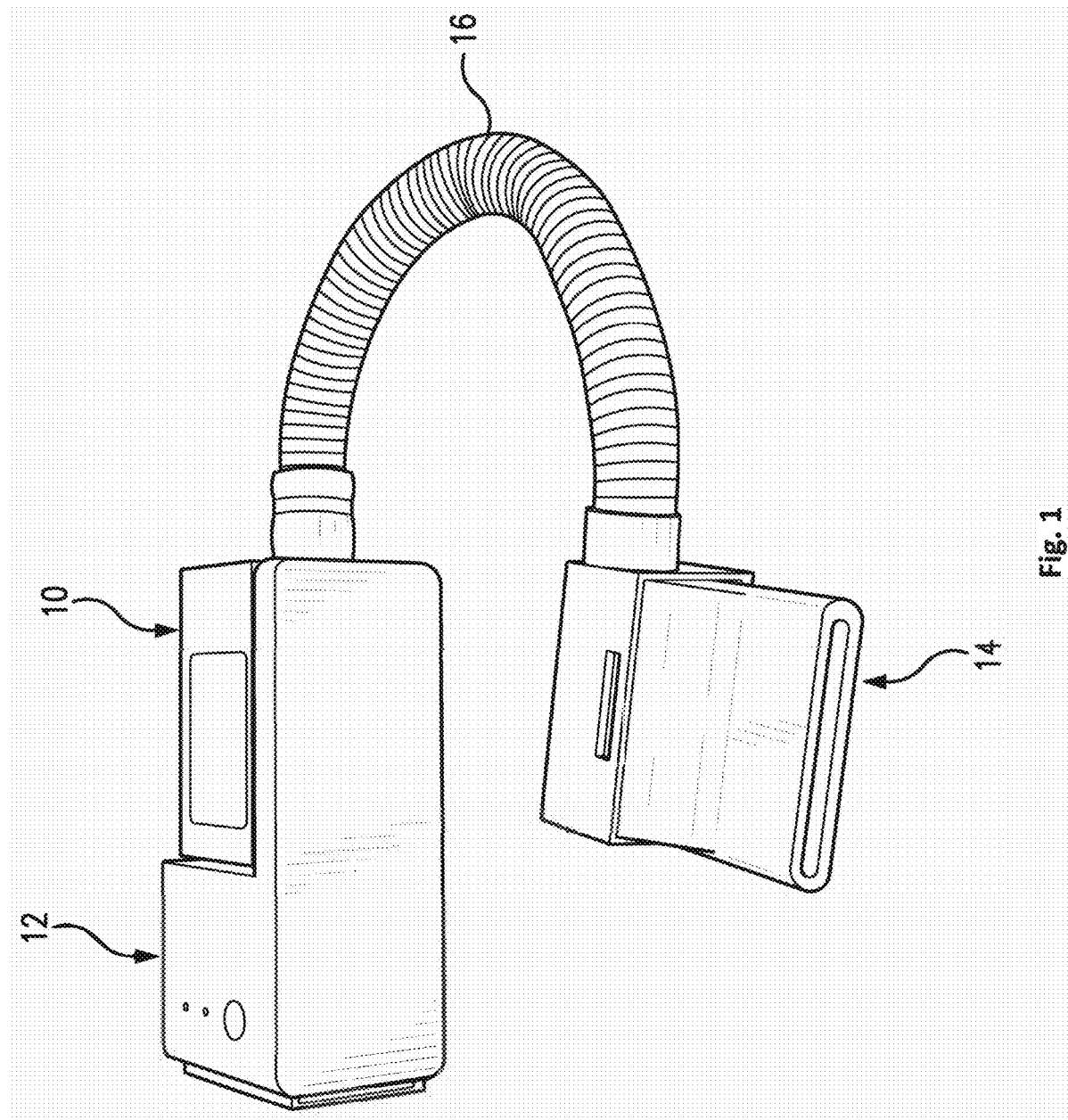
FIG. 1 is a perspective view of one embodiment of the assembly of the present invention in an assembled form.

The present invention is directed to an assembly for filtering odors issuing from a toilet bowl, including one or more embodiments which are operative to filter/remove odors from air and/or aerosolized fluid or "toilet plume", resulting from the toilet being flushed. As described hereinafter in greater detail, different ones of a possible plurality of embodiments of the filtering assembly may be structurally and operatively adapted for use in either a domestic environment or commercial environment and/or both.

Therefore, with primary reference to FIGS. 1-5 at least one preferred embodiment of the filtering assembly is generally indicated as 10 and comprises a first housing 12 and a second housing 14. As schematically represented in FIGS. 2A-2B, the first housing 12 is disposed in spaced relation to the toilet bowl 100, such as being mounted on the water tank 102 operatively associated with the toilet bowl 100. In addition, the second housing 14 is adapted to be removably mounted and/or supported on an outer peripheral rim 100' of the toilet bowl 100 in immediately adjacent, fluid communicating relation with the interior 103 of the toilet bowl 100. The operative positioning of the second housing 14 may vary, such as being mounted on a side portion of the toilet bowl 100, as represented in FIG. 2A and/or on a rear portion of the toilet bowl 100, substantially adjacent the connecting area 105 of a toilet seat 106, as represented in FIG. 2B.

Figure 2A:
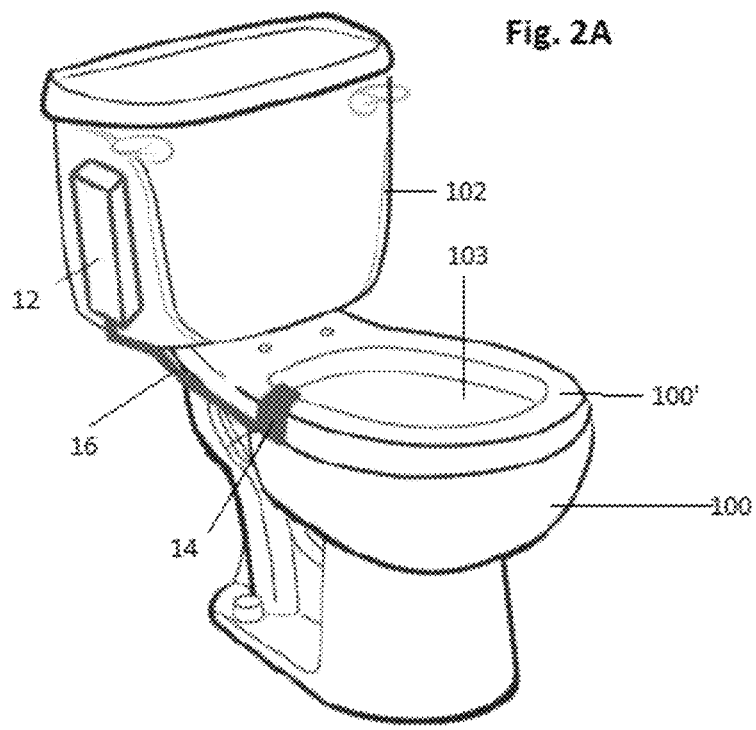
FIG. 2A is a schematic representation of the assembly of the embodiment of FIG. 1 in one operative position.
Figure 2B:
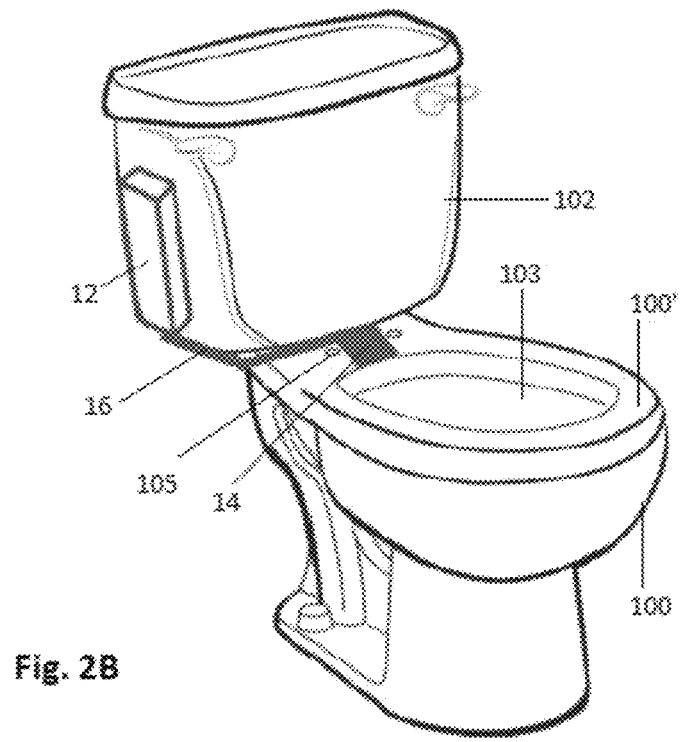
FIG. 2B is a schematic representation of the assembly of the embodiment of FIG. 1 in a different operative position from that represented in FIG. 2A.

The filtering assembly 10 further includes an elongated, preferably flexible material conduit 16 disposed in interconnecting, fluid communicating relation with the interiors of both the first housing 12 and the second housing 14. As demonstrated, the length and flexibility of the conduit 16 may also vary so as to facilitate selective dispositioning and mounting of the second housing 14 in different operative locations on the outer/upper periphery 100' of the toilet bowl 100, as represented in FIGS. 2A-2B. In order to facilitate shipping, storage, installation, maintenance, etc. of the filtering assembly 10, the conduit 16 is removably connected to both the first and second housing 12 and 14 respectively.

Also, the first and second housings 12 and 14 may be removably but securely disposed in different operative positions on the toilet bowl 100 and water tank 102 utilizing an adhesive, or other appropriate connecting structure. Such an adhesive or other connecting structure is preferably disposed on or directly associated with under or rear surface portions of the first and second housings 12 and 14, which engage the water tank 102 and toilet bowl periphery 100', respectively.

With primary reference to FIG. 3, structural and operative features of the first housing 12 includes an at least partially hollow interior appropriately dimensioned to enclose a plurality of operative components. More specifically, the first housing 12 includes a fan assembly generally indicated as 18 comprising at least one but alternatively a plurality of fan units 20. As represented, the one or more fan units 20 are operatively disposed to direct fluid from the interior of the first housing 12 and conduit 16 outwardly to an exterior of the first housing 12 into the area or space surrounding the toilet 100. As indicated, the conduit 16 is removably connected to the first housing 12 by an appropriate fitting 16', such that the interior the conduit 16 is disposed in direct fluid communication with the interior the first housing 12.

Additional structural components within the first housing 12 includes control circuitry generally indicated as 24 which may be in the form of a printed circuit board or other appropriate circuitry, which in turn may be powered by a battery 26 or in the alternative by an AC power source (not shown). Because of the structural and operative versatility of the filtering assembly 10 including, but not limited to, it being battery-powered as well as its ease-of-use, installation, maintenance, etc., as set forth above, the filtering assembly 10 may be suited for use in a home and/or domestic environment.

Also, in order to assure an adequate and effective filtering of fluid passing from the interior of the toilet bowl 100 through the filtering assembly 10, the first housing 12 may also include a secondary filter 28 to be used in conjunction with a primary filter 36 in the second housing 14, both of which may be activated carbon as explained in greater detail hereinafter.

Accordingly, as primarily represented in FIGS. 4A-4C, the second housing 14 comprises a filter segment 30 and a connector segment 32 removably connected to one another such that the interiors thereof are disposed in direct fluid communication with one another. In addition, the filter segment 30 includes an air/fluid inlet 34 formed at and at least partially defining an outer end of the filter segment 30. Also, a primary filter structure 36 is fixedly disposed within the interior of the filter segment 30 in direct fluid communication with fluid passing into the interior of the filter segment 30 through the inlet 34.

The connector segment 32 includes an appropriate fitting as at 16" which facilitates a removable connection to a corresponding end of the conduit 16. As such, when the filter assembly 10 is assembled as represented in at least FIGS. 1 and 2A-2B, the interior of the elongated conduit 16 is disposed in direct fluid communication with the interior of the second housing 14 including the interiors of both the removably connected filter segment 30 and the connector segment 32 and the interior of the first housing 12.

Further, the removable connection between the filter segment 30 and the connector segment 32 of the second housing 14 may be defined by a substantially telescopic and/or snap-fit connection as represented in both FIGS. 4A-4B. As such, the inner end of the filter segment 30 may be at least partially flexible so as to at least partially pass into the interior of the open inner end 32' of the connector segment 32. Further, the inner end of the filter segment 30 includes fixation ribs or like structures 38 disposed, dimensioned and configured to be removably received within a correspondingly disposed apertures or recesses 38' formed adjacent the inner end 32' of the connector segment 32. The flexibility of at least the inner end portion of the filter segment 30 will result in the one or more fixation ribs 38 being "snap-fit" into the correspondingly disposed one or more recesses 38'.

The removable connection of the filter segment 30 from the connector segment 32 facilitates the connector segment 32 and the filter 36 contained therein being accurately described as a replaceable, "single-use" filter medium. More specifically, after a predetermined period of use, the filter 36 may require replacement in order to efficiently operate. Replacement of the filter 36 is accomplished by removal of the second housing 14 from its operative position (see FIGS. 2A-2B) and the subsequent detachment of the filter segment 30 from the connector segment 32. Once detached, the filter segment 30 and the filter 36 fixedly retain therein are collectively structured for disposal. Thereafter, a new or replacement filter segment 30 and fixedly retained filter 36 may be reattached to the connector segment 32 for continued use of the filter assembly 10, once the second housing 14 is disposed in the intended operative position.

Accordingly, once completely assembled and disposed in the intended operative position as represented in FIG. 2A or FIG. 2B, a path of fluid flow is defined and/or established from the inlet 34 of the filter segment 30 of the second housing 14 through the filter 36, the interior of the connector segment 32, along the length of the interior of the conduit 16, into and through the first housing 12, through the secondary filter 28 and out of the first housing 12, through the fan assembly 18, comprising the one or more fan units 20.

Additive features of the filter assembly 10 may comprise the inclusion of additional fragrance or scent materials 40 disposed in one or both the first and second housings 12 and 14 as clearly represented in at least FIGS. 4B and 4C.

Figure 5:
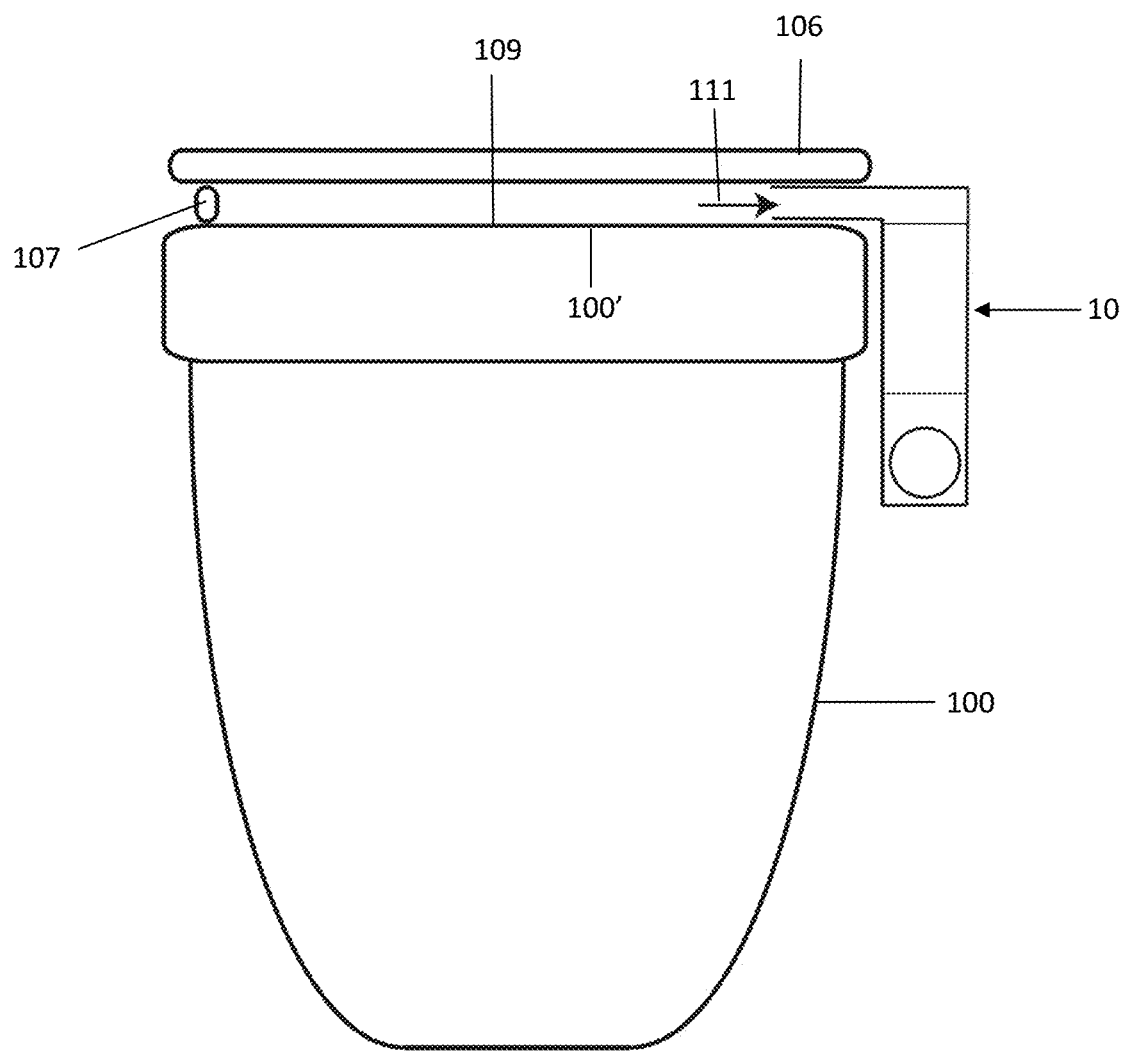
FIG. 5 is a front elevational view in schematic form of one operative position of the embodiment of FIGS. 4A-4C.

In order to assure proper operative placement of the second housing 14 in direct, fluid communicating relation with the interior 103 of the toilet bowl 100, an outer end 14' of the filter segment 14 is appropriately dimensioned and configured to fit within a clearance space 109, beneath a closed seat 106 associated with the toilet bowl 100, as schematically represented in FIG. 5. For purposes of clarity the filter assembly 10, specifically including the second housing 14, is not accurately oriented in order to properly represent the spacing 109 between the toilet seat 106 and the upper or outer periphery 100'.

As commonly structured and utilized, the toilet seat 106 in spaced above the periphery 100' due to the provision of the one or more bumpers 107, typically attached to the undersurface of the toilet seat 106. In cooperation therewith and with reference to FIG. 4A the outer end 14' of the filter segment 14 in the area contiguous and/or adjacent to the inlet 34 has a reduced "height" 14", preferably in the range of generally about 13 mm. As such the reduced height of the outer end 14' of the filter segment 14 is sufficiently dimensioned and configured to fit within the space 109 between the toilet seat 106 and the outer periphery 100', in direct fluid communication with the interior 103 of the toilet bowl 100, as schematically represented by directional arrow 111.

With primary reference to FIGS. 2C and 2D, another embodiment of the filtering assembly is generally indicated as 210 and is structurally distinguishable from the above noted filtering assembly embodiment 10, but operationally similar, as described in detail hereinafter. More specifically, the filtering assembly 210 comprises a first housing 212 which, is structured to be connected and/or removably connected to the aforementioned second housing 14, via the conduit 16. Further, when operatively disposed relative to the toilet bowl 100, the first housing 212 may be mounted on or adjacent to the water tank 102. However, due to the operative features of a sterilizing assembly 270, disposition of the first housing 212 may vary, as also described in greater detail hereinafter.

As with the embodiment of FIGS. 1, 2A, 2B, 3, and 4A-4C the first housing 212 includes a fan assembly 218 mounted within the interior thereof and disposed in communication with the exterior thereof, operatively similar to the embodiment of FIG. 3. Also, a filter 228 is disposed within the interior of the first housing 212 upstream of the fan assembly 218 and downstream of a connection fitting 16' to which the conduit 16 may be fixedly or removably attached. As with embodiments set forth above, filter 228 may be carbon/HEPA filter. Also, operative control circuitry may also be disposed within the interior of the first housing 212 and may be disposed and structured in a manner operatively similar to the control circuitry 24 in the embodiment of FIG. 3.

Moreover, the embodiment 210 of the filtering assembly may also include a sensor assembly 274 such as, but not limited to, a motion sensor. The sensor assembly 274 may be preferably mounted on an appropriate, exposed part of the first housing 212 and be so positioned/oriented to detect the presence of an individual using the toilet bowl 100. The sensor assembly 274 may be further structured to activate the fan assembly 218 while an individual remains in a predetermined detection zone, associated with the use of the toilet bowl 100. Automatic shutoff of the fan assembly to 18 may result upon an absence of an individual from the aforementioned detection zone.

One feature of the filtering assembly embodiment 210 includes a fluid sterilizing assembly which may be disposed along and in communicating relation with a path of fluid flow 120 generally within the first housing 212 and/or at least connected thereto. The fluid sterilizing assembly 270 comprises a UV light source 272, preferably operative within a bandwidth which is not harmful to human skin or eyes. Accordingly, a preferred operative bandwidth of the UV light source 272 is generally about 222 nm. However, it is noted that the operative bandwidth of the UV light source 272 may be such as to facilitate sterilization while not being harmful to human skin, eyes, etc. Further, the preferred UV light source may be operatively associated with a band filter window, wherein UV light issued there from is within the preferred bandwidth range of generally about 222 nm. It is recognized that this bandwidth is capable of killing pathogens and is therefore operative as fluid sterilizing source. It is also recognized that the preferred operative bandwidth of generally about 222 nm is different from a perhaps more conventional UV light of 254 nm, which may also be used as a sterilizing source, but may otherwise be harmful.

Operative and structural features of the sterilizing assembly 270 includes a reflector structure disposed relative to the UV light source 272 so as to direct a UV source of light both into and along the path of travel 120, as at 280 and exteriorly of the first housing 212 as at 282. Therefore, the reflector structure 273 may be at least partially formed from a high UV reflectance material such as, but not limited to, polytetrafluoroethylene (PTFE) and specifically configured, to direct at least a portion of the UV light as at 280 generated by the UV light source 272 onto fluid passing along the path of fluid flow 120 as it enters into the interior of the first housing 212. Concurrently, the reflector structure 273 is disposed dimensioned and configured to direct a second portion of the UV light source, as at 282, exteriorly of the housing 212.

The second portion 282 of the generated UV light source may therefore be directed onto portions of the toilet bowl 100, the seat 106, toilet handle and/or a floor or supporting surface surrounding and/or in the vicinity of the toilet bowl 100. The exposure of these of these surfaces or areas on the exterior of the first housing 212 facilitates the sterilization thereof due to exposure thereof to the second or exteriorly generated UV light source 282. Further, while not specifically represented, the reflector structure 273 may have a parabolic configuration or be otherwise sufficiently disposed, configured and dimensioned to concurrently reflect UV light from the UV light source 272 into at least an interior portion of the first housing 212 and along the path of fluid flow 120, as at 280, as well as exteriorly thereof, as at 282, onto areas or surface portions exterior of the first housing 212.

As set forth above, the first housing 212 may be connected on an exterior of the water tank 102 or generally adjacent thereof such that the reflected UV light source, as at 282 is directed onto the aforementioned intended exposed surfaces or areas exteriorly of the first housing 212. Therefore, an attachment structure as at 286 may be appropriately structured and disposed on a portion of the first housing 212 so as to mount, support and position the first housing 212 in an appropriate location such that the exteriorly directed UV light source 282 falls onto predetermined exterior surfaces or areas relative to the toilet bowl 100.

When the additional embodiment of FIGS. 2C and 2D, is operatively assembled by a fluid connection of the first housing 212 and a second housing 14, via conduit 16, the aforementioned path of fluid flow 120 is at least partially defined by and extends along from the inlet 34 of the second housing 14 through an interior of the second housing 14, along the length of the conduit 16 into the interior of the first housing 212, generally as at 16' and filtered to 28 and outwardly to the exterior of said first housing 212, concurrent to activation of the fan assembly 218.

Figure 6:
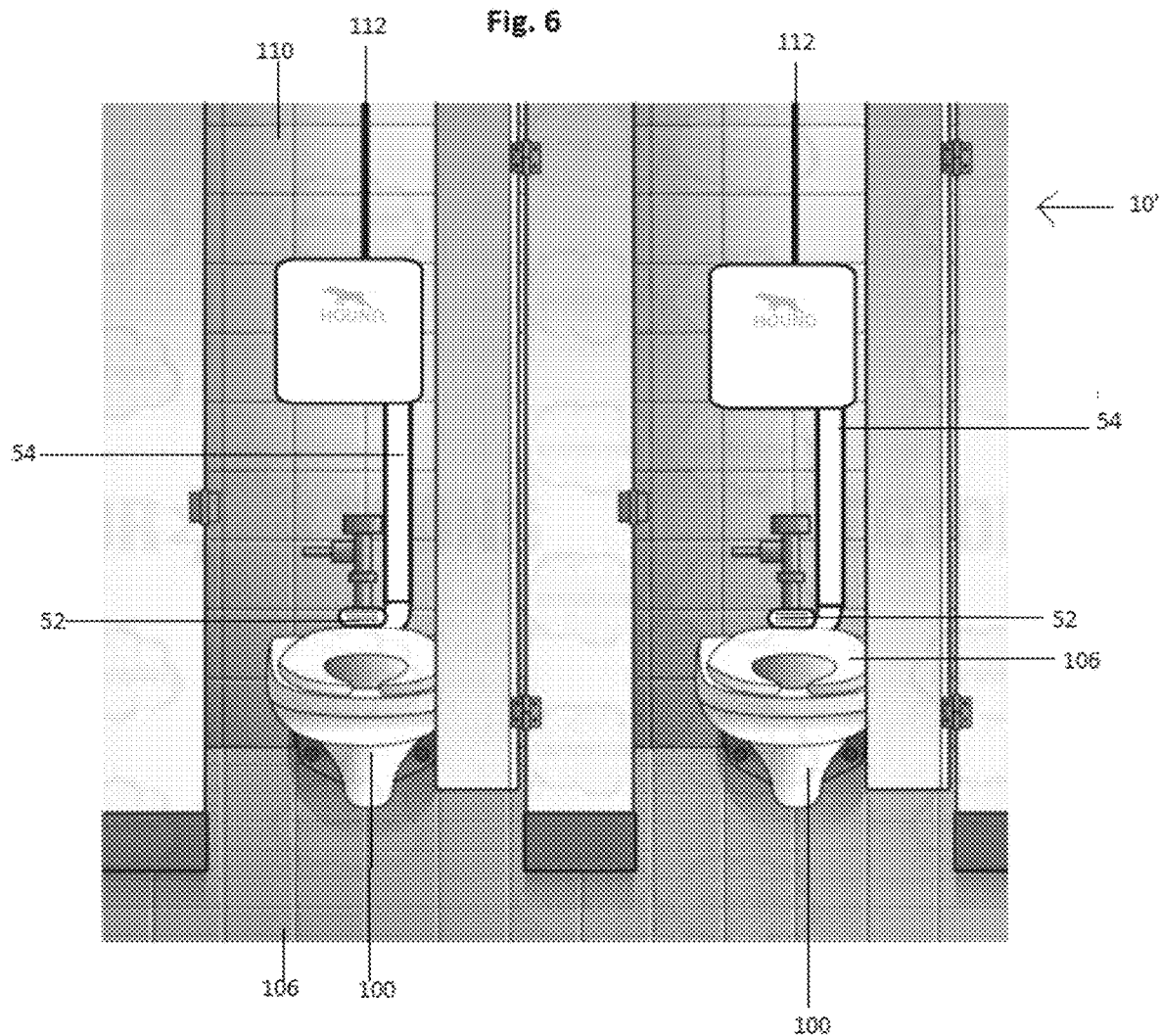
FIG. 6 is a perspective view of yet another embodiment of the assembly of the present invention operatively positioned at different toilet structures.

As represented in FIGS. 6-9, one or more additional embodiments of the present invention may include a filter assembly 10', structurally and operatively similar to the above-described embodiment of the filter assembly 10, but may be more adapted for use in a commercial environment, as represented in FIG. 6. As such, the at least one additional embodiment of the present invention includes the filter assembly 10' having a first housing 50 disposed in spaced relation to the toilet bowl 100 and also in spaced relation to a second housing 52. When in a commercial environment, the first housing 50 may be mounted on an exposed surface of a wall 110 adjacent to the toilet bowl 100. Further, because of its operative disposition in a commercial environment the filtering assembly 10' may be powered by a conventional AC power supply via a wired connection 112. As also represented in FIG. 6, the filtering assembly 10' includes an elongated conduit 54 disposed in interconnecting, fluid communicating relation between the interiors of the first housing 50 and the second housing 52. As such, the elongated conduit 54 may be operatively similar to the conduit 16 of the above-described filtering assembly 10.

Figure 7:
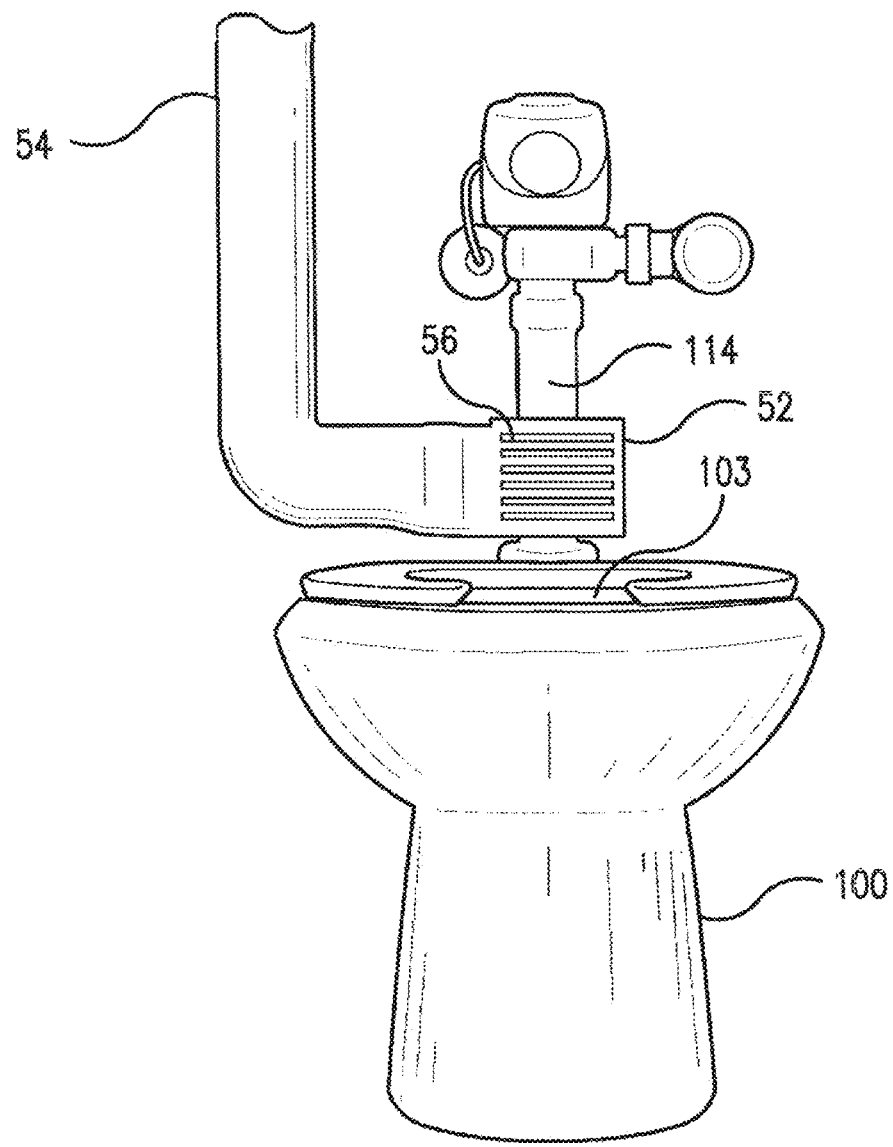
FIG. 7 is a front perspective view in partial cutaway of a portion of the embodiment of the assembly as represented in FIG. 6.

With primary reference to FIG. 7, the second housing 52 includes an inlet 56 operatively disposed immediately adjacent an interior 103 of the toilet bowl 100, such that the inlet 56 is in fluid receiving, fluid communicating relation with the interior 103 of the toilet bowl 100. In order to provide stability, the second housing 52 may be connected to or otherwise supported by a water pipe and/or plumbing fixture 114 associated with the toilet bowl 100 and operative to facilitate the flushing thereof.

As represented in FIGS. 8 and 9, the first housing 50 includes a filter assembly generally indicated as 58, contained therein. In addition, a fan assembly generally indicated as 60 is mounted within the first housing 50 in fluid communication with the conduit 54 and through the conduit 50, in fluid communication with the interior of the second housing 52 and the inlet 56 associated therewith. Therefore, the fan assembly 58, when activated, is disposed and structured to direct fluid flow 120 exiting the conduit 54, through the interior of the first housing 50 and outwardly therefrom to an exterior of the first housing 50, as schematically represented by directional arrows 120', subsequent to being filtered by filter assembly 58. Accordingly, an activation of the fan assembly 60, within the interior of the first housing 50, defines or establishes a path of fluid flow 120 extending from said inlet 56 of the second housing 52, through the conduit 54 and into the interior of the first housing 50, through the filter assembly 58, to the exterior of the first housing 50 and back into the space, area or environment surrounding the toilet bowl 100.

Yet additional features of the additional one or more embodiments of the filter assembly 10', which may render it more adaptable for use in a commercial environment, comprise the filter assembly 58 including a first filter unit 64 and a second filter unit 66, both located in the path of fluid flow 120, upstream of the conduit 54 and downstream of the fan assembly 60. The first filter unit 64 may be a carbon-based and/or carbon activated filter, primarily operative to remove odors from air/gas passing there through. The second filter unit 66 of the filter assembly 58 is preferably structured to process aerosolized fluid and any particulate matter contained therein. As such the second filter unit 66 may comprise an HEPA filter. As indicated, aerosolized fluid may result from the toilet being flushed and the creation of a "toilet plume", possibly containing odor causing particulate waste material.

It is also noted and recognized that the inlet 56 of the second housing 52 is disposed immediately adjacent and preferably exteriorly of the interior 103 of the toilet bowl 100. Accordingly, the fan assembly 60 is adequately powered and otherwise structured to expose the interior 103 of the toilet bowl 100 to a sufficiently strong fluid flow, to "draw" and/or collect aerosolized fluid along the path of fluid flow 120, from the interior 103 of the toilet bowl 100, through the inlet 56 and through the conduit 54, into the interior of the first housing 50, through the filter assembly 58 and outwardly from the exterior of the first housing 50.

In addition to the filter assembly 58 including, the first and second filter units 64 and 66 respectively, a fluid sterilizing assembly 70 may be disposed along the path of fluid flow 120, within the first housing 50, upstream of the conduit 54 and downstream of the fan assembly 60. The sterilizing assembly 70 may comprise at least one or in the alternative a plurality of ultraviolet (UV) lights 72 disposed in the aforementioned path of fluid flow 120 exiting from the filter assembly 58, or otherwise passing through the interior of the first housing 50.

Possible installation and use of this additional embodiment of the filter assembly 10' of the present invention may include a sensor assembly 74 such as, but not limited to, a motion sensor. The sensor assembly 74 may be preferably mounted on and at least partially exposed location on the first housing 50 facing a frontal portion of the toilet bowl 100 and be so positioned/oriented to detect the presence of an individual utilizing the toilet bowl 100. The sensor assembly 74 may be further structured to activate the fan assembly 60 while an individual remains in a predetermined detection zone, associated with the use of the toilet bowl 100. Automatic shutoff of the fan assembly 60 will result upon an absence of an individual from the aforementioned detection zone. Powering of the fan assembly 60 may best be accomplished by the direct wired connection 112 to the conventional AC power source, typically associated with most commercial locations, which include restrooms and or semi-public toilet facilities. Interconnection of the fan assembly 60, sensor assembly 74, one or more light units 72 and other electrically powered structures of the filter assembly 10' may be accomplished by appropriate control circuitry such as, but not limited to, printed circuitry 24, as described above with reference to the filtering assembly 10.

As a possible additive feature, a fragrance scent dispensing device or structure 40' may be included within the interior of the first housing 50 similar to the fragrance or scent dispensing structure 40 of the embodiment of FIGS. 4B and 4C.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:
1. An assembly for filtering toilet bowl orders comprising:
a first housing disposed in fluid communicating relation with an interior of the toilet bowl,
a fan assembly disposed within said first housing in communicating relation with an exterior thereof,
a filter disposed within said the first housing along a path of fluid flow from the interior of the toilet bowl to an interior of said first housing,
said path the fluid flow extending into and through said first housing to an exterior thereof, concurrent to activation of said fan assembly,
a sterilizing assembly connected to said first housing and including a UV light source; said UV light source operative at a bandwidth in a range destructive to pathogens, and
said sterilizing assembly disposed and structured to direct UV light from said UV light source concurrently onto said path of fluid flow and an exterior of said first housing.

2. The assembly as recited in claim 1 wherein said sterilizing assembly further comprises a reflector structure disposed adjacent and in light reflecting relation to said UV light source.

3. The assembly as recited in claim 2 wherein said reflector structure is disposed and configured to reflect UV light from said UV light source concurrently onto said path of fluid flow and said exterior of said housing.

4. The assembly as recited in claim 3 wherein said reflector structure is at least partially formed of a UV reflectance material.

5. The assembly as recited in claim 1 wherein said bandwidth of said UV light source is generally about 222 nm.

6. The assembly as recited in claim 1 wherein said sterilizing assembly, including said UV light source, is disposed upstream of said filter.

7. The assembly as recited in claim 6 wherein said fan assembly is disposed downstream of said filter.

8. The assembly as recited in claim 1 further comprising a second housing including an inlet, said inlet disposed in fluid communication with the interior of the toilet bowl.

9. The assembly as recited in claim 8 further comprising a conduit disposed in interconnecting, fluid communicating relation between said first and second housings.

10. The assembly as recited in claim 9 wherein said path of fluid flow is at least partially defined by and extends from said inlet, through an interior of said second housing, along a length of said conduit, the interior of said first housing, said filter, to the exterior of said first housing, concurrent to activation of said fan assembly.

11. The assembly as recited in claim 8 wherein said second housing comprises a filter segment including an outer end contiguous to said inlet; said outer end dimensioned and configured for operative disposition in removable, supported relation on a rim of the toilet bowl, beneath a closed seat thereof.

12. The assembly as recited in claim 11 wherein said first housing is disposed on an exterior of a water tank operatively associated with the toilet bowl, in interconnected relation to said second housing, via said conduit.

13. The assembly as recited in claim 1 further comprising a sensor assembly mounted on said first housing and structured and disposed to determine the use of the toilet bowl by an individual.

14. The assembly as recited in claim 13 wherein said sensor assembly comprises a motion sensor.

15. The assembly as recited in claim 1 wherein said filter is structured to process particulates in aerosolized fluid and odor passing there through.

16. The assembly as recited in claim 1 wherein said filter comprises an HEPA filter.

17. The assembly as recited in claim 1 further comprising a second housing including an inlet, said inlet disposed in fluid communication with an interior of the toilet bowl.

18. The assembly as recited in claim 17 further comprising an elongated conduit disposed in interconnecting, fluid communicating relation between interiors of said first housing and said second housing.

19. The assembly as recited in claim 17 wherein said second housing includes a filter segment and a connector segment removably connected to one another; said filter segment disposed and retaining relation to a filter.

20. The assembly as recited in claim 19 wherein said path of fluid flow is at least partially defined by and extends along said inlet, through said second housing, along a length of said conduit, into and through said filter within said first housing and to the exterior of said first housing, concurrent to activation of said fan assembly.

\* \* \* \* \*